(12) United States Patent
Okabe et al.

(10) Patent No.: US 7,863,255 B2
(45) Date of Patent: Jan. 4, 2011

(54) METHODS OF ADMINISTERING ANTITUMOR AGENT COMPRISING DEOXYCYTIDINE DERIVATIVE

(75) Inventors: Hiroyuki Okabe, Tokyo (JP); Kazuhito Arakawa, Tokyo (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 69 days.

(21) Appl. No.: 12/111,369

(22) Filed: Apr. 29, 2008

(65) Prior Publication Data

US 2009/0270340 A1    Oct. 29, 2009

(51) Int. Cl.
*A01N 43/04* (2006.01)
*A61K 31/70* (2006.01)

(52) U.S. Cl. .............................. 514/49; 514/42; 514/43; 514/50; 514/51

(58) Field of Classification Search ........................ None
See application file for complete search history.

(56) References Cited

U.S. PATENT DOCUMENTS 5,616,567 A   4/1997   Sasaki et al.
5,654,420 A   8/1997   Matsuda et al.

FOREIGN PATENT DOCUMENTS

JP    2559917 B2    9/1996

OTHER PUBLICATIONS

Galmarini et al. Lancet Oncol. (2002), vol. 3, pp. 415-424.*
English language Abstract of JP 2559917 B2.
Matsuda et al., "Nucleosides and Nucleotides. 100. 2'-*C*-Cyano-2'-deoxy-1-β-D-arabinofuranosyl-cytosine (CNDAC): Design of a Potential Mechanism-Based DNA-Strand-Breaking Antineoplastic Nucleoside", *J. Med. Chem.*, vol. 34, pp. 2917-2919 (1991).
Azuma et al., "Nucleosides and Nucleotides. 122. 2'-*C*-Cyano-2'-deoxy-1-β-D-arabinofuranosylcytosine and Its Derivatives. A New Class of Nucleoside with a Broad Antitumor Spectrum", *J. Med. Chem.*, vol. 36, pp. 4183-4189 (1993).
Azuma et al., "2'-*C*-Cyano-2'-deoxy-1-β-D-arabino-pentofuranosylcytosine: A Novel Anticancer Nucleoside Analog that Causes Both DNA Strand Breaks and $G_2$ Arrest", *Molecular Pharmacology*, vol. 59, No. 4, pp. 725-731 (2001).
Azuma et al., "Cellular pharmacokinetics and pharmacodynamics of the deoxycytidine analog 2'-*C*-Cyano-2'-deoxy-1-β-D-*arabino*-pentofuranosylcytosine (CNDAC)", *Biochem.Pharmacol.*, vol. 61, pp. 1497-1507 (2001).
Therasse et al., "New Guidelines to Evaluate the Response to Treatment in Solid Tumors", *Journal of National Cancer Institute*, vol. 92, No. 3, pp. 205-216 (2000).

* cited by examiner

*Primary Examiner*—Patrick T Lewis
(74) *Attorney, Agent, or Firm*—Greenblum & Bernstein, P.L.C.

(57) ABSTRACT

Antitumor treatment regimens comprising: administering, to a patient diagnosed with cancer, an antitumor agent comprising 4-amino-1-(2-cyano-2-deoxy-β-D-arabinofuranosyl)-2(1H)-pyrimidinone, or a salt thereof, by way of continuous intravenous infusion, in an amount of 2.0 to 4.0 mg per $m^2$ total body surface area of the patient, of 4-amino-1-(2-cyano-2-deoxy-β-D-arabinofuranosyl)-2(1H)-pyrimidinone equivalent, per day, for a duration of 168 to 336 hours. Compositions for providing the methods are also disclosed.

8 Claims, 4 Drawing Sheets

METHODS OF ADMINISTERING ANTITUMOR AGENT COMPRISING DEOXYCYTIDINE DERIVATIVE

FIELD OF THE INVENTION

The present invention relates to an antitumor agent administered to cancer patients by intravenous infusion, and in some preferred embodiments, by continuous intravenous infusion.

BACKGROUND OF THE INVENTION 4-amino-1-(2-cyano-2-deoxy-β-D-arabinofuranosyl)-2 (1H)-pyrimidinone (CNDAC; See the Formula I below) is an antimetabolite in which the 2'-β position of deoxycytidine ribose is replaced by a cyano group.

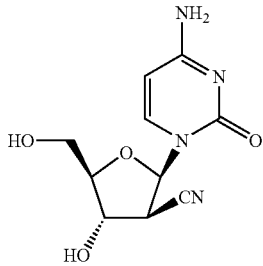

[Formula 1]

CNDAC is a deoxycytidine analog, which at the time of filing of this application, is synthesized in Japan. Unlike deoxycytidine derivatives (gemcitabine) which are widely clinically used, CNDAC primarily causes DNA strand breaks. Specifically, it is considered that CNDAC is phosphorylated by intracellular deoxycytidine kinase, and thereby a triphosphorylated form (CNDACTP) is provided; that CNDACTP is incorporated into a DNA strand, thus inducing hydrolysis and breaking the DNA strand; and that the cell cycle is thus arrested at the G2/M phase and the cell is killed. (See, for example, Japanese Patent Publication No. 2559917; J. Med. Chem., 1991, 34 (9): 2917-9; and J. Med. Chem., 1993, 36 (26): 4183-9.)

Most antitumor agents, which have an inhibitory effect on DNA synthesis as a main effect and are widely clinically used, demonstrate the effect as exhibiting the inhibitory effect at the S phase. Different from relatively fast-growing tumors used in animal tests, however, it has been identified that tumors grow slowly in clinical circumstances and that there are few cells in the S phase. Meanwhile, the antitumor effect of CNDAC, which is achieved by the DNA strand break effect, eventually arrests the cell cycle at the G2/M phase and thus kills tumor cells. Accordingly, it is considered that CNDAC can be differentiated from DNA synthesis inhibitors in wide clinical use, and that CNDAC is a clinically effective antitumor agent (Molecular Pharmacology, 2001, 59 (4): 725-31).

In order to achieve a higher antitumor effect of CNDAC for clinical use, it is necessary to develop a highly effective treatment method that enables continuous medication and surely prolongs patient survival.

SUMMARY OF THE INVENTION

The present invention solves the aforementioned problems by using CNDAC in a way that achieves a high antitumor effect and a low risk of causing toxicity that leads to interruption of continuous administration.

As a result of extensive research on a method of using CNDAC by the inventors of the present invention, it was found that a high antitumor effect was achieved when CNDAC was administered by continuous intravenous infusion for a long period of time, and thus that the method of use would be an effective method in helping to prolong patient survival.

The antitumor agent according to the present invention is capable of achieving a high antitumor effect while reducing risk of side effects, mainly including body weight suppression and leucopenia. In other words, the antitumor agent has a low risk of interrupting treatment due to side effects and provides a high treatment effect so as to surely prolong patient survival.

The invention provides, in some embodiments, an antitumor treatment regimen comprising: administering, to a patient diagnosed with cancer, an antitumor agent comprising 4-amino-1-(2-cyano-2-deoxy-β-D-arabinofuranosyl)-2 (1H)-pyrimidinone, or a salt thereof, by way of continuous intravenous infusion, in an amount of 2.0 to 4.0 mg per m$^2$ total body surface area of the patient, of 4-amino-1-(2-cyano-2-deoxy-β-D-arabinofuranosyl)-2(1H)-pyrimidinone equivalent, per day, for a duration of 168 to 336 hours. In some preferred embodiments, the antitumor agent is administered in an amount of 2.0 mg per m$^2$ total body surface area of the patient, of 4-amino-1-(2-cyano-2-deoxy-β-D-arabinofuranosyl)-2(1H)-pyrimidinone equivalent, per day, for a duration of 336 hours. In some preferred embodiments, the antitumor agent is administered in an amount of 3.0 mg per m$^2$ total body surface area of the patient, of 4-amino-1-(2-cyano-2-deoxy-β-D-arabinofuranosyl)-2(1H)-pyrimidinone equivalent, per day, for a duration of 168 hours. In some embodiments, a treatment course is performed at least twice, wherein the course comprises administering the antitumor agent by continuous intravenous infusion in an amount of 2.0 mg per m$^2$ total body surface area of the patient, of 4-amino-1-(2-cyano-2-deoxy-β-D-arabinofuranosyl)-2(1H)-pyrimidinone equivalent, per day, for a duration of 336 hours once every three weeks. In some embodiments, a treatment course is performed at least twice, wherein the course comprises administering the antitumor agent by continuous intravenous infusion in an amount of 3.0 mg per m$^2$ total body surface area of the patient, of 4-amino-1-(2-cyano-2-deoxy-β-D-arabinofuranosyl)-2(1H)-pyrimidinone equivalent, per day, for a duration of 168 hours once every two weeks.

The invention also provides a composition for continuous intravenous administration of an antitumor agent to a patient comprising a container comprising 4-amino-1-(2-cyano-2-deoxy-β3-D-arabinofuranosyl)-2(1H)-pyrimidinone, or a salt thereof, diluted in a physiologically acceptable fluid medium for delivering intravenous antitumor agents, to a concentration sufficient to provide an amount of 2.0 to 4.0 mg per m$^2$ total body surface area of the patient, of 4-amino-1-(2-cyano-2-deoxy-β-D-arabinofuranosyl)-2(1H)-pyrimidinone equivalent, per day, for a duration of 168 to 336 hours. In some preferred embodiments, the concentration of the antitumor agent is sufficient to provide an amount of 2.0 mg per m$^2$ total body surface area of the patient, of 4-amino-1-(2-cyano-2-deoxy-β-D-arabinofuranosyl)-2(1H)-pyrimidinone equivalent, per day, for a duration of 336 hours. In some preferred embodiments, the concentration of the antitumor agent is sufficient to provide an amount of 3.0 mg per m$^2$ total body surface area of the patient, of 4-amino-1-(2-cyano-2-deoxy-β-D-arabinofuranosyl)-2(1H)-pyrimidinone equivalent, per day, for a duration of 168 hours.

BRIEF DESCRIPTION OF THE FIGURES

The present invention is further described in the description of invention that follows, in reference to the noted plurality of non-limiting drawings, wherein.

DETAILED DESCRIPTION OF THE INVENTION

Figure 1:
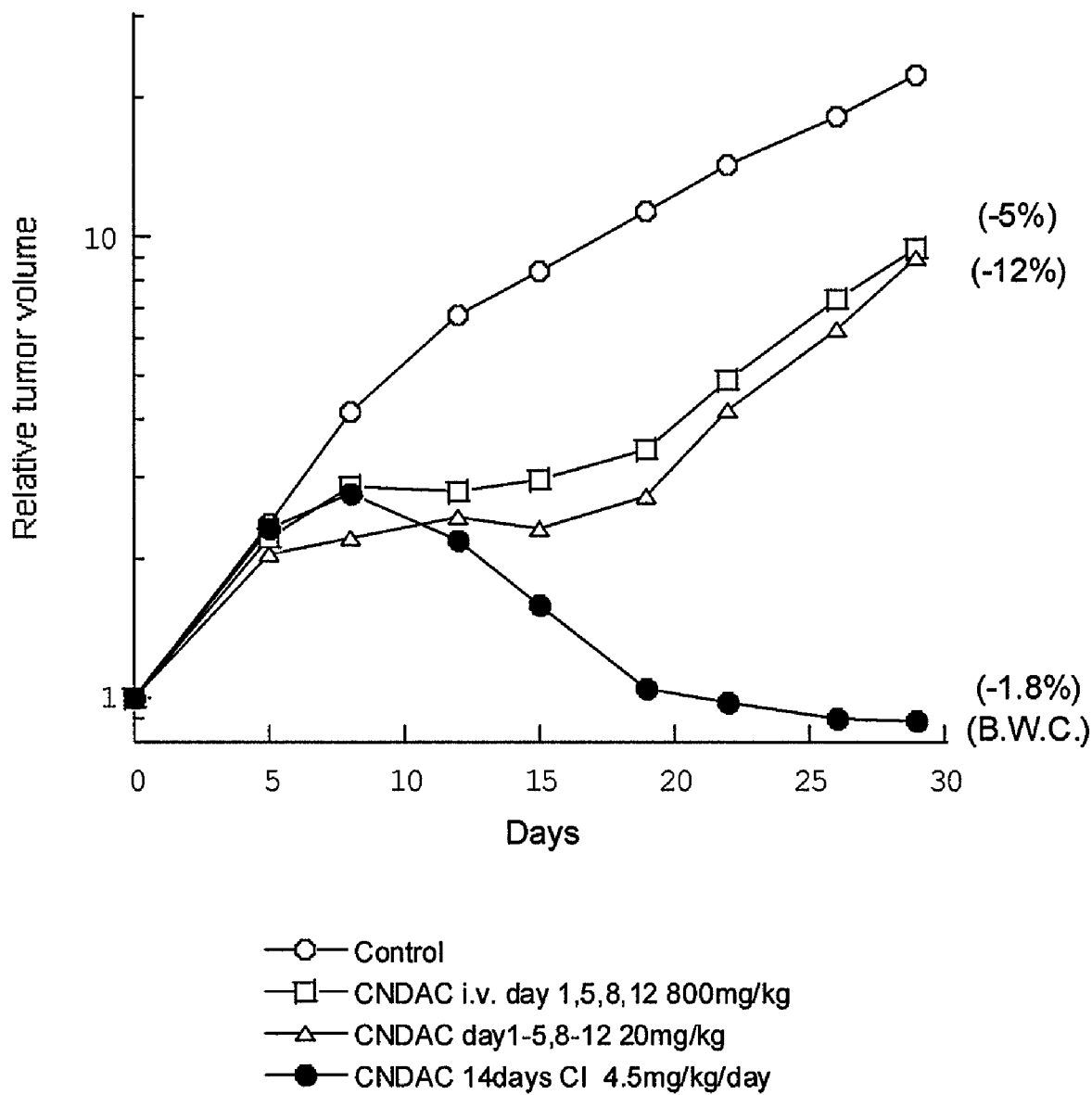
FIG. 1 shows the antitumor effect in rapid intravenous infusion and continuous intravenous infusion of CNDAC administered to tumor-bearing rats having the human lung cancer line LX-1.

Unless otherwise stated, a reference to a compound or component includes the compound or component by itself, as well as in combination with other compounds or components, such as mixtures of compounds.

As used herein, the singular forms "a," "an," and "the" include the plural reference unless the context clearly dictates otherwise.

Except where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not to be considered as an attempt to limit the application of the doctrine of equivalents to the scope of the claims, each numerical parameter should be construed in light of the number of significant digits and ordinary rounding conventions.

Additionally, the recitation of numerical ranges within this specification is considered to be a disclosure of all numerical values within that range. For example, if a range is from about 1 to about 50, it is deemed to include, for example, 1, 7, 34, 46.1, 23.7, or any other value within the range.

The present inventors have discovered that CNDAC exhibits a strong antitumor effect against a wide range of tumor lines. It was found in antitumor tests using animal models that CNDAC demonstrated strong antitumor and antiproliferative effects on a majority of human-derived tumor lines when administered by rapid intravenous infusion for 10 consecutive days, five times a week for two weeks, and once a week for two weeks. However, the regrowth of tumors was observed after completion of the administration, and the cytoreductive effect was not necessarily shown. Further, increasing the dosage so as to increase the antitumor effect causes toxicity, including body weight suppression and leucopenia.

As a result of extensive research on a method of using CNDAC by the inventors of the present invention, it was found that a high antitumor effect was achieved when CNDAC was administered by continuous intravenous infusion for a long period of time, and thus that the method of use would be an effective method in helping to prolong patient survival.

CNDAC, which is an active ingredient of the antitumor agent according to the present invention, is a known compound indicated as 4-amino-1-(2-cyano-2-deoxy-β-D-arabinofuranosyl)-2(1H)-pyrimidinone. It is known that the compound has an antitumor effect on many cancer types by its DNA strand break effect. It is described in Biochemical Pharmacology, 2001; 61 (12): 1497-507, that contacting CNDAC with tumor cells for a long time enhances the inhibitory effect on cell growth. It is not suggested, however, that cancer can be effectively treated while development of side effects is inhibited.

As a salt of CNDAC, any pharmaceutically acceptable salts can be used, such as, for example, inorganic and organic acid salts. Inorganic acid salts include hydrochloride, hydrobromate, sulfate, nitrate, phosphate, and the like. Organic acid salts include acetate, propionate, tartrate, fumarate, maleate, malate, citrate, methanesulfonate, p-toluenesulfonate, trifluoroacetate, and the like. Among the salts above, hydrochloride or acetate is preferable.

CNDAC according to the present invention and the salt thereof can be manufactured by any method, examples of which are known, such as, for example, a method described in Japanese Patent Publication No. 2559917.

The antitumor agent according to the present invention is administered intravenously. The agent is administered in form of injections. Injections may be liquid injections or solid injections, such as, lyophilized injections, which are dissolved when used, powder injections, and the like.

The antitumor agent according to the present invention can be prepared in any procedure, examples of which are known, in which pharmacologically acceptable carriers are added to CNDAC or the salt thereof. A variety of organic and inorganic carrier materials commonly used as pharmaceutical materials can be used as the carriers. For solid injections, excipients, lubricants, binders, disintegrants, and the like can be added. For liquid injections, diluents, auxiliary dissolvents, suspenders, tonicity agents, pH adjusters, buffers, stabilizers, soothing agents, and the like can be added. In addition, pharmaceutical additives, such as antiseptics, antioxidants, colorants, and the like, can be used when necessary.

Excipients may include, for example, lactose, sucrose, sodium chloride, glucose, maltose, mannitol, erythritol, xylitol, maltitol, inositol, dextran, sorbitol, albumin, urea, starch, calcium carbonate, kaolin, crystalline cellulose, silicic acid, methylcellulose, glycerin, alginate sodium, gum arabic, and mixtures of the above-listed ingredients. Lubricants may include, for example, purified talc, stearate, borax, polyethyleneglycol, and mixtures of the above-listed ingredients. Binders may include, for example, simple syrups, dextrose solutions, starch solutions, gelatin solutions, polyvinyl alcohol, polyvinyl ether, polyvinylpyrrolidone, carboxymethylcellulose, shellac, methylcellulose, ethylcellulose, water, ethanol, potassium phosphate, and mixtures of the above-listed ingredients. Disintegrants may include, for example, dry starch, alginate sodium, powdered agar, powdered laminaran, sodium hydrogen carbonate, calcium carbonate, polyoxyethylene sorbitan fatty acid esters, sodium lauryl sulfate, monoglyceride stearate, starch, lactose, and mixtures of the above-listed ingredients. Diluents may include, for example, water, ethyl alcohol, macrogol, propylene glycol, ethoxylated isostearyl alcohol, polyoxidized isostearyl alcohol, polyoxyethylene sorbitan fatty acid esters, and mixtures of the above-listed ingredients. Stabilizers may include, for example, sodium pyrosulfite, ethylenediaminetetraacetic acid, thioglycolic acid, thiolactic acid, and mixtures of the above-listed ingredients. Tonicity agents may include, for example, sodium chloride, boric acid, glucose, glycerin, and mixtures of the above-listed ingredients. PH adjusters and buffers may include, for example, sodium citrate, citric acids, sodium acetate, sodium phosphate, and mixtures of the above-listed ingredients. Soothing agents may include, for example, procaine hydrochloride, lidocaine hydrochloride, and mixtures of the above-listed ingredients.

A preferable dosage of the antitumor agent according to the present invention is 2.0 to 3.0 mg per $m^2$ total body surface area of the patient (also presented herein as $mg/m^2$) of CNDAC equivalent per day, in terms of a relation between the risk of side-effects development and antitumor effect.

In view of effective cancer treatment with inhibition of side-effects development, including body weight suppression and leucopenia, it is preferable to administer the antitumor agent of the present invention for a duration of 168 to 336 hours when the dosage per day is 2.0 $mg/m^2$ of CNDAC equivalent. It is more preferable to administer the antitumor agent for a duration of 336 hours. When the dosage per day is 3.0 $mg/m^2$ of CNDAC equivalent, it is preferable to administer the antitumor agent for a duration of 168 hours.

In order to reduce toxicity and achieve a better antitumor effect, it is preferable to administer the antitumor agent of the present invention intravenously in a repeated manner in a course of a series of administration schedule. A preferable administration schedule is that a course is performed, one time or a plurality of repeated times, in which the antitumor agent is administered by continuous intravenous infusion in an amount of 2.0 to 4.0 $mg/m^2$ of CNDAC equivalent per day for a duration of 336 hours once every three weeks; and that a course is performed, one time or a plurality of repeated times, in which the antitumor agent is administered by continuous intravenous infusion in an amount of 3.0 to 4.0 $mg/m^2$ of CNDAC equivalent per day for a duration of 168 hours once every two weeks. It is more preferable that a course is performed, one time or a plurality of repeated times, in which the antitumor agent is administered by continuous intravenous infusion in an amount of 2.0 $mg/m^2$ of CNDAC equivalent per day for a duration of 336 hours once every three weeks; and that a course is performed, one time or a plurality of repeated times, in which the antitumor agent is administered by continuous intravenous infusion in an amount of 3.0 $mg/m^2$ of CNDAC equivalent per day for a duration of 168 hours once every two weeks.

The antitumor agent of the present invention can be applied to non-limiting cancer types, including head and neck cancer, esophagus cancer, stomach cancer, colorectal cancer, liver cancer, gallbladder and bile duct cancer, pancreatic cancer, lung cancer, breast cancer, ovarian cancer, bladder cancer, prostate cancer, testis tumor, bone and soft-tissue sarcoma, malignant lymphoma, leukemia, cervical cancer, skin cancer, brain tumor, and the like. It is particularly preferable to apply the antitumor agent to head and neck cancer, breast cancer, lung cancer, stomach cancer, colorectal cancer, pancreatic cancer, and bladder cancer.

The antitumor agent of the present invention may be administered to patients who have never undergone cancer treatment, currently treated patients, and previously treated patients.

The antitumor agent of the present invention can be administered concurrently with other antitumor agents and/or radiation. Antitumor agents that can be administered concurrently may include, for example, 5-FU, tegafur/uracil preparations, tegafur/gimeracil/oteracil potassium preparations, doxorubicin, epirubicin, irinotecan hydrochloride, etoposide, docetaxel, paclitaxel, cisplatin, carboplatin, oxaliplatin, krestin, lentinan, picibanil, and the like.

EXAMPLES

It is to be understood that while the invention has been described in conjunction with certain preferred and/or specific embodiments, the foregoing description as well as the examples that follow are intended to illustrate and not limit the scope of the invention. Other aspects, advantages, and modifications within the scope of the invention will be apparent to those skilled in the art to which the invention pertains.

All chemical reagents referred to in the appended examples are commercially available unless otherwise indicated.

Example 1

The frequency of adverse events and treatment effect were studied in a case where a course was repeatedly performed in which the antitumor agent was administered to cancer patients by continuous intravenous infusion in an amount of 2.0 to 4.0 $mg/m^2$ of CNDAC (free base) for a duration of 336 hours once every three weeks.

The present test was conducted on patients having a variety of solid cancers for which standard treatment was ineffective or no treatment was available (e.g., digestive system cancer, head and neck cancer, breast cancer, and the like). The test is equivalent to the Clinical Phase I Test, which primarily evaluates safety so as to determine a recommended dose (RD) that can be safely administered with no side effect concerns in the Clinical Phase II Test implemented per cancer type. Treatment effect on tumors was also evaluated in the test when possible. In the treatment effect test, the cytoreductive effect was determined based on comprehensive evaluation of target lesions (lesions having a size measurable at a slice width on CT and a larger size) and non-target lesions (all lesions not included in the target lesions), with reference to the RECIST evaluation method (Journal of the National Cancer Institute, 2000, Vol. 92, No. 3, 205-216). In the present test, PR (partial response) indicates a case where a reduction of 30% or more in the sum of the longest diameter of target lesions was demonstrated, compared with the sum of the longest diameter of pre-administration; the effect was maintained for a predetermined period (normally four weeks); and non-target lesions did not exacerbate during the period. PD (progression disease) indicates a case where an increase of 20% or more in the sum of the longest diameter of target lesions was demonstrated, compared with the smallest sum of the longest diameter recorded since the start of the test; or existing non-target lesions obviously exacerbated, or new lesions were recognized. SD (stable disease) indicates a case where reduction of tumors was not enough to be determined as PR, but insufficient to be determined as PD; and the progression of tumors stopped and no exacerbation was observed.

As results of administration of a continuous intravenous infusion of CNDAC preparations (injection) in an amount of 2.0 to 4.0 $mg/m^2$ for a duration of 336 hours once every three weeks, dose limiting toxicity (DLT) was observed in three out of three cases (100%) (febrile neutropenia of CTCAE Grade 3 in all cases; platelet reduction of Grade 4 in one out of the three cases) when 4.0 $mg/m^2$ was administered, and thus administration of a minimum of two courses as defined in the implementation plan could not be completed. Further, although DLT was not observed when 3.0 $mg/m^2$ was administered, neutropenia of Grades 3 and 4 was found in the second case each of two courses, and thus the dosage needed to be reduced in one case. The efficacy (SD) was demonstrated in one out of the three cases. Meanwhile, when 2.0 mg/M² was administered, no adverse event was seen that required interruption of the administration. SD was demonstrated in four out of six cases (66%), for which the efficacy could be evaluated, and one case among the cases demonstrated a reduction of about 15%.

Accordingly, it was concluded in the CNDAC administration that continuous intravenous infusion was an administration method that achieved a high efficacy while inhibiting toxicity development, the continuous intravenous infusion being administered to patients having a variety of solid cancers (e.g., digestive system cancer, lung cancer, bladder cancer, and the like) for which standard treatment was ineffective or no treatment was available.

Example 2

The frequency of adverse events and treatment effect were studied in a case where a course was repeatedly performed in which the antitumor agent was administered by continuous intravenous infusion in an amount of 3.0 to 4.0 mg CNDAC (free base) per square meter of body surface area for a duration of 168 hours once every two weeks. Tested patients, evaluation methods, and evaluation standards are the same as those in the test in Example 1.

As results of administration of a continuous intravenous infusion of CNDAC preparations (injection) in an amount of 3.0 to 4.0 mg/m² for a duration of 168 hours once every two weeks, when 4.0 mg/m² was administered, dose limiting toxicity (DLT) was observed in two out of three cases (67%), for which the safety could be evaluated (febrile neutropenia of CTCAE Grade 3 in one case; neutropenia of Grade 4 in one case). The efficacy (SD) was demonstrated in two out of the three cases (67%), for which the safety could be evaluated. Meanwhile, when 3.0 mg/m² was administered, no adverse event was seen that required interruption of the administration. SD was demonstrated in two out of eight cases (25%), for which the efficacy could be evaluated.

Accordingly, it was concluded in the CNDAC administration that continuous intravenous infusion was an administration method that achieved a high efficacy while inhibiting toxicity development, the continuous intravenous infusion being administered to patients having a variety of solid cancers (e.g., digestive system cancer, and head and neck cancer) for which standard treatment was ineffective or no treatment was available.

Example 3

The antitumor effect was studied in rapid intravenous infusion and continuous intravenous infusion of CNDAC in tumor-bearing rat models. FIG. 1 indicates the study results of the antitumor effect in rapid intravenous infusion and continuous intravenous infusion of CNDAC administered to tumor-bearing rats having the human lung cancer line LX-1.

CNDAC (free base) was administered by rapid intravenous infusion (rapidly injected into a caudal vein using a syringe) in an amount of 800 mg/kg/day on Days 1, 5, 8, and 12, or 20 mg/kg/day on Days 1 to 5 and 8 to 12. Alternatively, CNDAC was administered by continuous intravenous infusion (continuously injected under the skin for 24 hours using a subcutaneous implantation constant-speed pump) in an amount of 4.5 mg/kg/day for two weeks. Relative tumor volume (a ratio of tumor volume on Day 1 of administration and that on Day 14 of administration) was obtained in a CNDAC administered group and a non-administered group (control group) of each administration method, and the obtained relative tumor volume was compared. A high antitumor effect was demonstrated in the continuous intravenous infusion, compared with the rapid intravenous infusion. The effect was exhibited not only in the human lung cancer line, but also in human breast cancer and colon cancer lines.

Example 4

Figure 2:
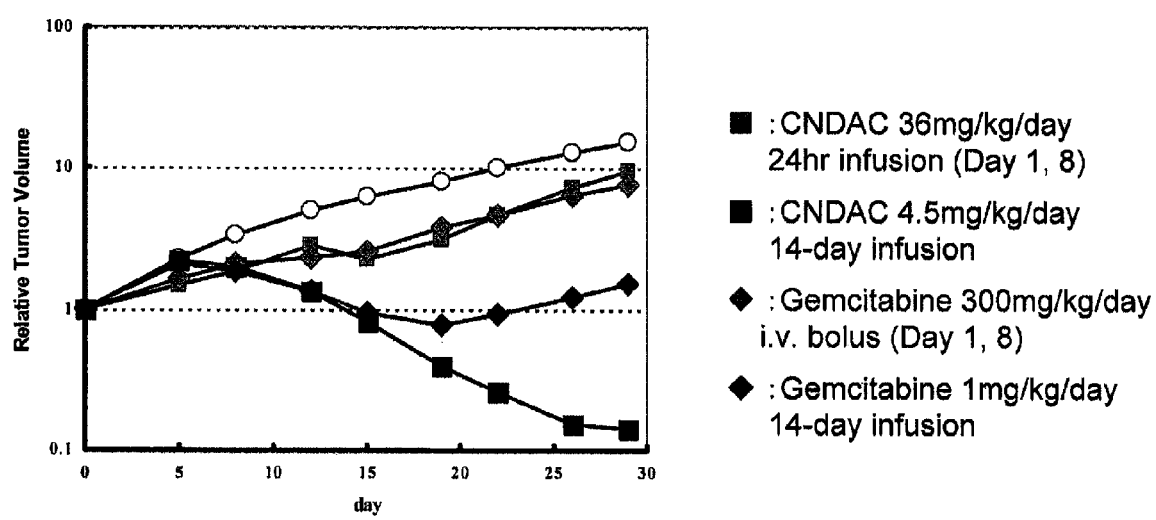
FIG. 2 shows the antitumor effect in continuous intravenous infusion of CNDAC and gemcitabine administered to tumor-bearing rats having the human colon cancer line KM20C.

The antitumor effect was studied in a continuous intravenous infusion of CNDAC and gemcitabine administered to tumor-bearing rats having the human colon cancer line KM20C. FIG. 2 indicates the results.

CNDAC was administered by continuous intravenous infusion (continuously injected under the skin for 24 hours using a subcutaneous implantation constant-speed pump) in an amount of 36 mg/kg/day on Days 1 and 8, or 4.5 mg/kg/day on Days 1 to 14. Alternatively, gemcitabine was administered by rapid intravenous infusion in an amount of 300 mg/kg/day once a week for two weeks (Days 1 and 8), or by continuous intravenous infusion in an amount of 1.0 mg/kg/day for two weeks. Relative tumor volume was obtained and compared in a drug administered group and a non-administered group (control group) of each administration method. In the continuous intravenous infusion of CNDAC, the tumor volume was significantly reduced even after the administration was completed. In contrast, in the continuous intravenous infusion of gemcitabine, which is a deoxycytidine derivative having a similar structure as CNDAC, the tumor volume was not reduced after the administration was completed. The results indicate that administering CNDAC at low doses for a long period of time enhanced the antitumor effect extremely strongly beyond expectation, compared with the enhancement by gemcitabine.

Example 5

Figure 3:
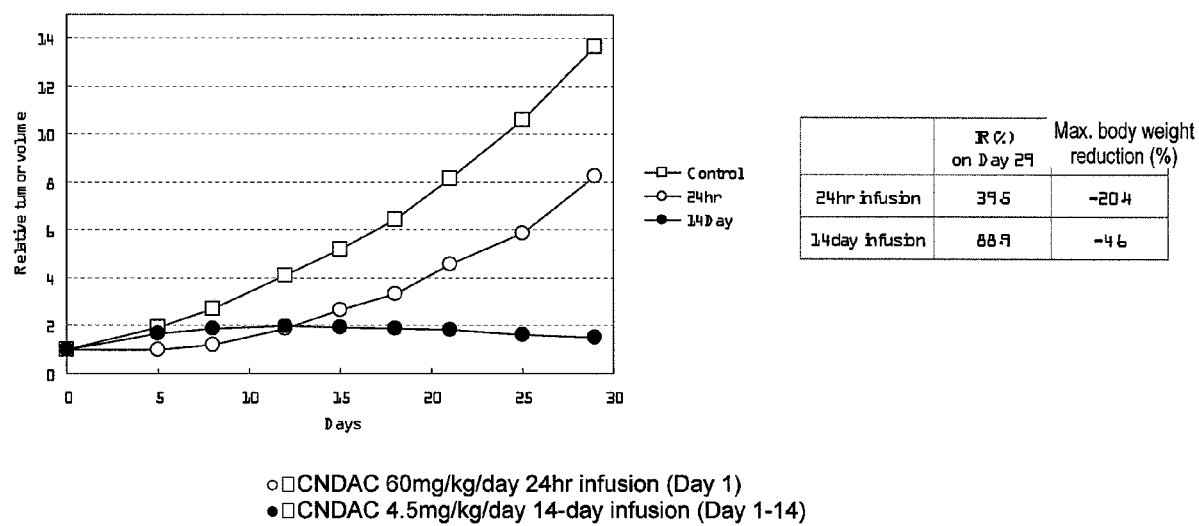
FIG. 3 shows the antitumor effect in continuous intravenous infusion of CNDAC administered to tumor-bearing rats having the human pancreatic cancer line PAN-4.
Figure 4:
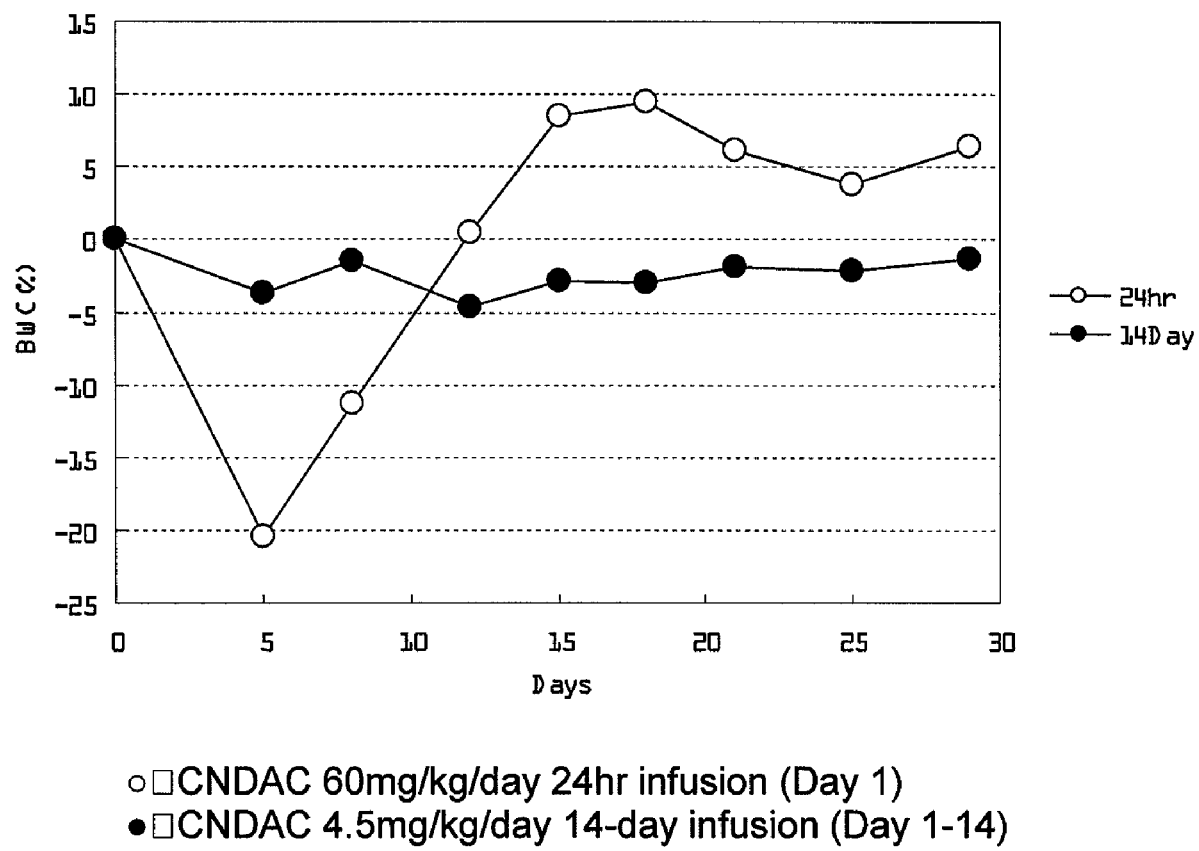
FIG. 4 shows side effect (body weight suppression) in continuous intravenous infusion of CNDAC administered to tumor-bearing rats having the human pancreatic cancer line PAN-4.

A relation between the antitumor effect and side effect (body weight suppression) was studied in a continuous intravenous infusion of CNDAC administered to tumor-bearing rats having the human pancreatic cancer line PAN-4. FIGS. 3 and 4 indicate the results.

CNDAC was administered by continuous intravenous infusion (continuously injected under the skin for 24 hours using a subcutaneous implantation constant-speed pump) in an amount of 36 mg/kg/day on Day 1, or 4.5 mg/kg/day on Days 1 to 14. Relative tumor volume was obtained and compared in a CNDAC administered group and a non-administered group (control group) of each administration method. A significantly high antitumor effect was demonstrated in the two-week continuous intravenous infusion, compared with the 24-hour continuous intravenous infusion.

Further, body weight reduction in the two-week continuous intravenous infusion group and 24-hour continuous intravenous infusion group was studied. A body weight reduction of as much as 20.4% at maximum was confirmed in the 24-hour continuous intravenous infusion group, while the body weight reduction was 4.6% even at maximum in the two-week continuous intravenous infusion. The results indicate that the long-term continuous intravenous infusion provided a significantly high antitumor effect while sufficiently reducing the side effect (body weight reduction).

The specification is most thoroughly understood in light of the teachings of the documents cited within the specification, all of which are hereby incorporated by reference in their entirety. The embodiments within the specification provide an illustration of embodiments of the invention and should not be construed to limit the scope of the invention. The skilled artisan recognizes that many other embodiments are encompassed by the claimed invention and that it is intended that the specification and examples be considered as exemplary only, with a true scope and spirit of the invention being indicated by the following claims.

What is claimed is:

1. An antitumor treatment regimen comprising: administering, to a patient diagnosed with cancer, an antitumor agent comprising 4-amino-1-(2-cyano-2-deoxy-β-D-arabinofuranosyl)-2(1H)-pyrimidinone, or a salt thereof, by way of continuous intravenous infusion, in an amount of 2.0 to 4.0 mg per $m^2$ total body surface area of the patient, of 4-amino-1-(2-cyano-2-deoxy-β-D-arabinofuranosyl)-2(1H)-pyrimidinone equivalent, per day, for a duration of 168 to 336 hours.

2. The antitumor treatment regimen according to claim 1, wherein the antitumor agent is administered in an amount of 2.0 mg per $m^2$ total body surface area of the patient, of 4-amino-1-(2-cyano-2-deoxy-β-D-arabinofuranosyl)-2(1H)-pyrimidinone equivalent, per day, for a duration of 336 hours.

3. The antitumor treatment regimen according to claim 1, wherein the antitumor agent is administered in an amount of 3.0 mg per $m^2$ total body surface area of the patient, of 4-amino-1-(2-cyano-2-deoxy-β-D-arabinofuranosyl)-2(1H)-pyrimidinone equivalent, per day, for a duration of 168 hours.

4. The antitumor treatment regimen according to claim 1, wherein a treatment course is performed at least twice, wherein the course comprises administering the antitumor agent by continuous intravenous infusion in an amount of 2.0 mg per $m^2$ total body surface area of the patient, of 4-amino-1-(2-cyano-2-deoxy-β-D-arabinofuranosyl)-2(1H)-pyrimidinone equivalent, per day, for a duration of 336 hours once every three weeks.

5. The antitumor treatment regimen according to claim 1, wherein a treatment course is performed at least twice, wherein the course comprises administering the antitumor agent by continuous intravenous infusion in an amount of 3.0 mg per $m^2$ total body surface area of the patient, of 4-amino-1-(2-cyano-2-deoxy-β-D-arabinofuranosyl)-2(1H)-pyrimidinone equivalent, per day, for a duration of 168 hours once every two weeks.

6. A composition for continuous intravenous administration of an antitumor agent to a patient comprising a container comprising 4-amino-1-(2-cyano-2-deoxy-β-D-arabinofuranosyl)-2(1H)-pyrimidinone, or a salt thereof, diluted in a physiologically acceptable fluid medium for delivering intravenous antitumor agents, to a concentration sufficient to provide an amount of 2.0 to 4.0 mg/$m^2$ of 4-amino-1-(2-cyano-2-deoxy-β-D-arabinofuranosyl)-2(1H)-pyrimidinone equivalent, per day, for a duration of 168 to 336 hours.

7. The composition for continuous intravenous administration of an antitumor agent according to claim 6, wherein the concentration of the antitumor agent is sufficient to provide an amount of 2.0 mg per $m^2$ total body surface area of the patient, of 4-amino-1-(2-cyano-2-deoxy-β-D-arabinofuranosyl)-2(1H)-pyrimidinone equivalent, per day, for a duration of 336 hours.

8. The composition for continuous intravenous administration of an antitumor agent according to claim 6, wherein the concentration of the antitumor agent is sufficient to provide an amount of 3.0 mg per $m^2$ total body surface area of the patient, of 4-amino-1-(2-cyano-2-deoxy-β-D-arabinofuranosyl)-2(1H)-pyrimidinone equivalent, per day, for a duration of 168 hours.

* * * * *